US012774933B2

(12) United States Patent
Mostovov

(10) Patent No.: US 12,774,933 B2
(45) Date of Patent: Oct. 27, 2026

(54) CALIBRATING DEVICE AND METHOD FOR INSOLE

(71) Applicant: RXFUNCTION, INC., Eden Prairie, MN (US)

(72) Inventor: Andrey Mostovov, Paris (FR)

(73) Assignee: RXFUNCTION, INC., Eden Prairie, MN (US)

( * ) Notice: Subject to any disclaimer, the term of this patent is extended or adjusted under 35 U.S.C. 154(b) by 238 days.

(21) Appl. No.: 18/558,820

(22) PCT Filed: May 5, 2022

(86) PCT No.: PCT/EP2022/062103
§ 371 (c)(1),
(2) Date: Nov. 3, 2023

(87) PCT Pub. No.: WO2022/233996
PCT Pub. Date: Nov. 10, 2022

(65) Prior Publication Data

US 2024/0230446 A1 Jul. 11, 2024

(30) Foreign Application Priority Data

May 6, 2021 (EP) .................................... 21305585

(51) Int. Cl.
*G01L 25/00* (2006.01)
*A61B 5/00* (2006.01)
(Continued)

(52) U.S. Cl.
CPC ............ *G01L 25/00* (2013.01); *A61B 5/1038* (2013.01); *G01L 1/146* (2013.01); *A61B 5/6807* (2013.01);
(Continued)

(58) Field of Classification Search
CPC ....... G01L 25/00; G01L 1/146; G01L 27/002; A61B 5/1038; A61B 5/6807;
(Continued)

(56) References Cited

U.S. PATENT DOCUMENTS

| | | | |
|---|---|---|---|
| 1,540,430 | A | 6/1925 | William |
| 1,658,170 | A | 2/1928 | La Chapelle |

(Continued)

FOREIGN PATENT DOCUMENTS

| | | | |
|---|---|---|---|
| CN | 109655373 | A | 4/2019 |
| CN | 109945775 | A | 6/2019 |

(Continued)

OTHER PUBLICATIONS

Sorrentino et al., "A Novel Sensorised Insole for Sensing Feet Pressure Distributions", arxiv.org, Cornell University Library, Oct. 14, 2019, 21 pages.

(Continued)

*Primary Examiner* — Brandi N Hopkins
(74) *Attorney, Agent, or Firm* — Fredrikson & Byron, P.A

(57) ABSTRACT

A calibrating device for pressure sensors, allowing for calibration of pressure sensors with a well-controlled increase rate of pressure. The calibrating device includes a calibration chamber configured to allow placing a sample pressure sensor inside, reference pressure sensor to measure pressure inside the calibration chamber, and a gas source. Also, a method for calibration of pressure sensors.

15 Claims, 2 Drawing Sheets

(51) Int. Cl.
*A61B 5/103* (2006.01)
*G01L 1/14* (2006.01)

(52) U.S. Cl.
CPC ................. *A61B 2560/0223* (2013.01); *A61B 2562/0247* (2013.01)

(58) Field of Classification Search
CPC .... A61B 2560/0223; A61B 2562/0247; G01N 33/0022; G01N 33/007; G01N 30/32; G01N 27/4163; G01F 25/17; G01F 1/6847; G01F 25/10; G01F 1/42; C01B 21/203; A61M 1/281; H01J 49/26; A61H 9/00; A43B 17/03; Y02B 30/70; G01M 3/3281
See application file for complete search history.

(56) References Cited

U.S. PATENT DOCUMENTS

| | | | | |
|---|---|---|---|---|
| 3,881,496 | A | 5/1975 | Vredenbregt et al. | |
| 4,510,699 | A | 4/1985 | Nakamura et al. | |
| 4,569,352 | A | 2/1986 | Petrofsky et al. | |
| 4,745,930 | A | 5/1988 | Confer | |
| 4,760,850 | A | 8/1988 | Phillips et al. | |
| 4,813,436 | A | 3/1989 | Au | |
| 5,121,747 | A | 6/1992 | Andrews | |
| 5,253,510 | A | 10/1993 | Allen et al. | |
| 5,551,445 | A | 9/1996 | Nashner | |
| D382,995 | S | 9/1997 | Hale | |
| 5,678,448 | A | 10/1997 | Fullen et al. | |
| 5,790,256 | A | 8/1998 | Brown et al. | |
| 5,896,608 | A | 4/1999 | Whatley | |
| 5,919,149 | A | 7/1999 | Allum | |
| 5,979,067 | A | 11/1999 | Waters | |
| 6,063,046 | A | 5/2000 | Allum | |
| 6,174,294 | B1 | 1/2001 | Crabb et al. | |
| 6,273,863 | B1 | 8/2001 | Avni et al. | |
| 6,389,883 | B1 | 5/2002 | Berme et al. | |
| D467,408 | S | 12/2002 | Chen | |
| 6,505,522 | B1 | 1/2003 | Wilssens | |
| D496,155 | S | 9/2004 | Londono | |
| 6,788,976 | B2 | 9/2004 | Gesotti | |
| 6,832,987 | B2 | 12/2004 | David et al. | |
| 6,978,684 | B2 | 12/2005 | Nurse | |
| 7,124,628 | B2 * | 10/2006 | Wildman | F02M 65/00 73/114.51 |
| D536,867 | S | 2/2007 | Sexson | |
| D537,623 | S | 3/2007 | Dennis et al. | |
| 7,403,821 | B2 | 7/2008 | Haugland et al. | |
| D625,204 | S | 10/2010 | Kimura | |
| 7,883,479 | B1 | 2/2011 | Stanley et al. | |
| D637,918 | S | 5/2011 | Cobbett et al. | |
| D640,143 | S | 6/2011 | Virgili | |
| 7,998,092 | B2 | 8/2011 | Avni et al. | |
| 8,151,487 | B2 | 4/2012 | Mclinden | |
| 8,209,036 | B2 | 6/2012 | Nathan et al. | |
| D672,127 | S | 12/2012 | Walker | |
| 8,556,830 | B2 | 10/2013 | Sherman et al. | |
| 8,597,210 | B2 | 12/2013 | Sherman et al. | |
| 8,694,110 | B2 | 4/2014 | Nathan et al. | |
| D724,556 | S | 3/2015 | Choi et al. | |
| 8,974,402 | B2 | 3/2015 | Oddsson et al. | |
| 9,289,174 | B2 | 3/2016 | Oddsson et al. | |
| 9,402,580 | B2 | 8/2016 | Oddsson et al. | |
| 10,178,970 | B2 | 1/2019 | Oddsson et al. | |
| 10,653,352 | B2 | 5/2020 | Oddsson et al. | |
| 11,451,931 | B1 | 9/2022 | Hariharan et al. | |
| 2002/0055779 | A1 | 5/2002 | Andrews | |
| 2003/0027118 | A1 | 2/2003 | Abraham-Fuchs et al. | |
| 2004/0059543 | A1 | 3/2004 | Abraham-Fuchs et al. | |
| 2005/0103092 | A1 | 5/2005 | Chiarito et al. | |
| 2005/0131317 | A1 | 6/2005 | Oddsson et al. | |
| 2009/0161653 | A1 | 6/2009 | Kumar et al. | |
| 2011/0299472 | A1 | 12/2011 | Kumar | |
| 2012/0188997 | A1 | 7/2012 | Zakrzewski et al. | |
| 2013/0118265 | A1 | 5/2013 | Besling et al. | |
| 2013/0215712 | A1 | 8/2013 | Geiser et al. | |
| 2013/0236867 | A1 | 9/2013 | Avni et al. | |
| 2014/0174224 | A1 | 6/2014 | Zhang | |
| 2014/0309534 | A1 | 10/2014 | Pichler et al. | |
| 2015/0025816 | A1 | 1/2015 | Ross | |
| 2015/0123802 | A1 | 5/2015 | Oddsson et al. | |
| 2016/0235557 | A1 | 8/2016 | Herr et al. | |
| 2016/0295589 | A1 | 10/2016 | Nikopour et al. | |
| 2017/0035329 | A1 | 2/2017 | Gavish | |
| 2017/0055880 | A1 | 3/2017 | Agrawal et al. | |
| 2017/0188950 | A1 | 7/2017 | Gazdag et al. | |
| 2017/0225033 | A1 | 8/2017 | Czaja | |
| 2017/0273599 | A1 | 9/2017 | Reese et al. | |
| 2017/0307376 | A1 | 10/2017 | Zihajehzadeh et al. | |
| 2018/0077663 | A1 | 3/2018 | Davis et al. | |
| 2019/0158202 | A1 | 5/2019 | Madine et al. | |
| 2019/0175107 | A1 | 6/2019 | Lu et al. | |
| 2019/0336040 | A1 | 11/2019 | Chang et al. | |
| 2020/0054931 | A1 | 2/2020 | Martin et al. | |
| 2020/0078638 | A1 | 3/2020 | Statham et al. | |
| 2020/0214595 | A1 | 7/2020 | Roberts et al. | |
| 2020/0318972 | A1 | 10/2020 | Couvet | |
| 2021/0382978 | A1 | 12/2021 | Jeon et al. | |
| 2022/0051779 | A1 | 2/2022 | Marcus et al. | |
| 2022/0299321 | A1 | 9/2022 | Zhao et al. | |
| 2022/0338759 | A1 | 10/2022 | Vidal et al. | |
| 2023/0260552 | A1 | 8/2023 | Bose et al. | |
| 2024/0230434 | A1 | 7/2024 | Jo et al. | |
| 2025/0344966 | A1 | 11/2025 | Zanotto et al. | |

FOREIGN PATENT DOCUMENTS

| | | | | |
|---|---|---|---|---|
| CN | 110049440 | A | 7/2019 | |
| EP | 1369677 | A1 * | 12/2003 | G01L 27/005 |
| EP | 2848908 | A1 | 3/2015 | |
| EP | 3340827 | A1 | 7/2018 | |
| EP | 3714785 | A1 | 9/2020 | |
| EP | 3731238 | A1 | 10/2020 | |
| JP | 2018114277 | A | 7/2018 | |
| WO | 2015183677 | A1 | 12/2015 | |
| WO | 2017033036 | A1 | 3/2017 | |
| WO | 2021213634 | A1 | 10/2021 | |
| WO | 2022101366 | A1 | 5/2022 | |

OTHER PUBLICATIONS

International Search Report and Written Opinion issued on Sep. 20, 2022, in corresponding International Application No. PCT/EP2022/062103, 7 pages.

Lidstone, et al., "Electronic measurement of plantar contact area during walking using an adaptive thresholding method for Medilogic pressure-measuring insoles ", The Foot, Elsevier, vol. 39, Jan. 17, 20219, XP085876938, ISSN: 0958-2592, pp. 1-10.

Veltink, P.H. (1999) Sensory Feedback in artificial control of human mobility. Technology and Health Care, 7(6), 383-391, https://doi.org/10.3233/thc-1999-7602 (Year:1999).

* cited by examiner

CALIBRATING DEVICE AND METHOD FOR INSOLE

FIELD

The present disclosure relates to a calibrating device for pressure sensors. In particular, the calibrating device allows for calibration of pressure sensors with a well-controlled increase rate of pressure.

BACKGROUND

In various fields, such as medical fields or sport training, it is often desirable to know the distribution of pressure forces exerted by a subject on an object, in a static or dynamic manner.

In particular in the medical field, plantar pressure monitoring could find applications in diagnostic podiatry, orthopedics or gait analysis. Usual systems use insoles comprising pressure sensors. These sensors are calibrated to define a relationship between pressure applied on the sensor and signal generated by sensor. Usually, these sensors comprise a plurality of pressure cells, each pressure cell acquiring pressure signal over a limited area of the sensor. Calibration thus means defining a relationship between pressure applied on the sensor and signal generated by each pressure cell.

In addition, pressure sensors used in medical field have dimensions comparable to the size of the body part under study. When insoles are used as pressure sensors, a typical dimension is from 20 cm to 30 cm (usual European sizes from 30 to 45). Usual calibration devices, in which position of the pressure sensor is controlled, have a limited size. There is then a need for calibrating devices allowing for calibration of a large pressure sensor.

Last, pressure sensors must be calibrated with well controlled conditions of constraint. Indeed, response of a pressure sensor may be different if constraint is applied very slowly (quasi static equilibrium) or very quickly, in a dynamic manner. A calibrating device enabling a control of the rate of constraint variation is thus desirable.

The calibrating device here disclosed overcomes some or all the drawbacks. Indeed, large pressure sensors may be calibrated. Calibration may be obtained in one single step even if the pressure sensor is large or comprises a plurality of pressure cells. Moreover, rate of variation of constraint on the pressure sensor may be controlled precisely.

SUMMARY

The present invention relates to a calibrating device for a sample pressure sensor comprising

- a calibration chamber having a constant dead volume $V_0$ in the range of 0.1 L to 1.5 L, said calibration chamber being gas tight;
- a reference pressure sensor configured to measure pressure inside the calibration chamber; and
- a gas source comprising a gas tank connected to the calibration chamber through a valve so as to inject a controlled flow of gas into the calibration chamber;
- wherein the valve comprises a flow controller having an equivalent inner diameter comprised between 2.5 mm and 3.5 mm.

In an embodiment, the calibration chamber further comprises a pressure switch and/or a safety valve.

In an embodiment, the calibration chamber has one longitudinal dimension longer than 30 cm, preferably one inner area with one longitudinal dimension longer than 30 cm and one perpendicular dimension wider than 10 cm.

In an embodiment, the calibration chamber further comprises a gas tight membrane configured to split the calibration chamber in two compartments, the first compartment comprising the reference pressure sensor and the second compartment being configured to receive a sample pressure sensor.

The present invention also relates to a method of calibration for a sample pressure sensor comprising the following steps:

- i) placing a sample pressure sensor inside a calibration chamber having a constant dead volume $V_0$ in the range of 0.1 L to 1.5 L, said calibration chamber being gas tight;
- ii) injecting gas from a gas source into the calibration chamber through a valve comprising a flow controller having an equivalent inner diameter comprised between 2.5 mm and 3.5 mm;
- iii) acquiring simultaneously pressure signal in the calibration chamber with a reference pressure sensor and output signal of the sample pressure sensor during injection of gas; and
- iv) determining the calibration function of the sample pressure sensor.

In an embodiment, a pressure switch controls venting of the calibration chamber when pressure inside the calibration chamber reaches a predetermined threshold during step ii).

In an embodiment, pressure signals of reference pressure sensor and sample pressure sensor are measured simultaneously at a frequency comprised between 50 Hz and 200 Hz, preferably between 100 Hz and 150 Hz, more preferably at about 110 Hz.

In an embodiment, the sample pressure sensor comprises a plurality of capacitive pressure cells and calibration function of the sample pressure sensor (S) comprises a calibration function of each capacitive pressure cell.

In an embodiment, the sample pressure sensor is an insole.

In an embodiment, a plurality of sample pressure sensors is placed inside the calibration chamber and a calibration function is determined for each sample pressure sensor.

In an embodiment, steps ii) and iii) are repeated and calibration function of the sample pressure sensor is determined from the successive pressure signals in the calibration chamber and successive output signals of the sample pressure sensor.

In an embodiment, gas is injected during step ii) at a constant pressure increase rate.

DETAILED DESCRIPTION

In the present invention, the following terms have the following meanings:

"Calibration function" refers to the function modelling the output signal of a sensor versus an applied constraint. In particular, the function may be a graph (an abacus), an array of discrete values or a mathematical function such as a polynomial function. If the sensor comprises a plurality of sensing cells, the calibration function of the sensor may be a combination of the calibration functions of each sensing cell, such as a weighted average, or a list of the calibration functions of each sensing cell.

"Dead volume" refers to the volume of a chamber that can be filled with gas. The dead volume is defined by the outer limits of the chamber—walls, valves—including volume of tubing used for valves, from which all solid components inside the limits of the chamber are subtracted, in particular the volume of the sample pressure sensor to be calibrated.

"Flow rate" refers to the volume of gas flowing through an element—in particular a valve or flow controller—during one second (in $L \cdot s^{-1}$). Flow rate varies with pressure difference between both side of said element. In this disclosure, flow rate of gas is measured for a pressure difference of 6 bars.

"Equivalent inner diameter" of a gas distribution element—in particular a valve or a flow controller—refers to the diameter of the constriction of a tube through which flow rate under a difference of 6 bars is the same as the flow rate through said element. For instance, an equivalent inner diameter of 2.5 mm corresponds to about 3.8 $L \cdot s^{-1}$ flow rate; an equivalent inner diameter of 3 mm corresponds to about 8 $L \cdot s^{-1}$ flow rate and an equivalent inner diameter of 3.5 mm corresponds to about 14.8 $L \cdot s^{-1}$ flow rate.

"Pressure cell" refers to the component of a pressure sensor that is modified by pressure. The modification may be evidenced on a physical property of the pressure cells: thickness, bending state, electrical resistance for resistive pressure sensors, electrical capacitance for capacitive pressure sensors.

"Pressure sensor" refers to a sensor that responses according to pressure applied on one or a plurality of pressure cells. The response (or output) may be the modification of a physical property of the pressure cells or an electric signal characterizing the pressure cells. In this disclosure, the reference pressure sensor is a calibrated sensor designed to measure pressure inside the calibration chamber, whereas the sample pressure sensor is a pressure sensor that needs to be calibrated. A pressure sensor may consist of one single pressure cell, or may comprise a plurality of pressure cells.

This disclosure relates to a calibrating device for a sample pressure sensor. The sample pressure sensor needs to be calibrated, i.e., the calibration function modelling the output signal of the sample pressure sensor versus pressure applied has to be determined.

Figure 1:
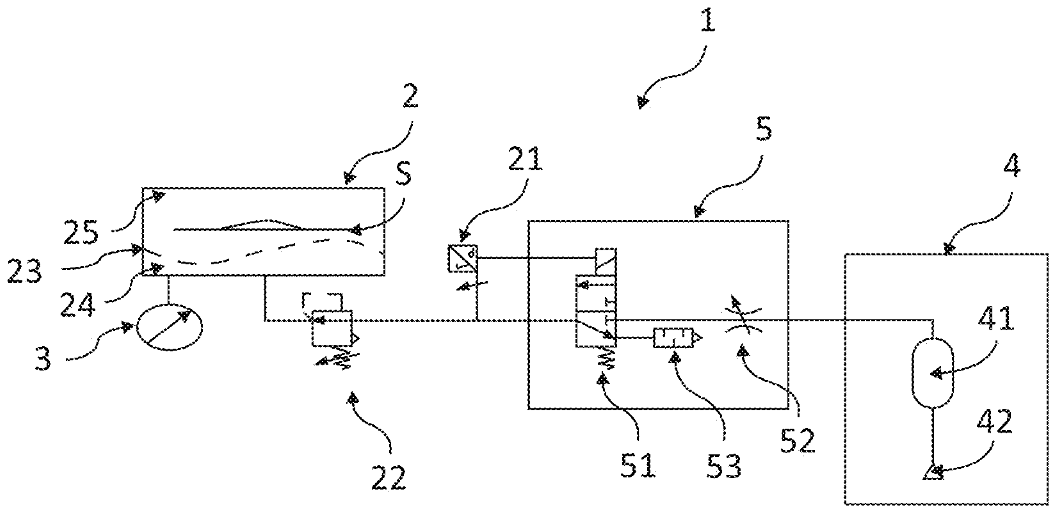
FIG. 1 shows an example of the calibrating device disclosed herein.

As illustrated on FIG. 1, the calibrating device 1 comprises a calibration chamber 2 having a constant dead volume $V_0$ in the range of 0.1 L to 1.5 L. By constant, it is meant that the calibration chamber 2 withstands pressure variation without deformation. The dead volume of the calibration chamber 2 is larger than 0.1 L so that a sample pressure sensor S suitable to be worn by a subject—a footwear like an insole, a glove, a strap—may be placed in the calibration chamber 2. The dead volume of the calibration chamber 2 is lower than 1.5 L so that calibrating device 1 remains compact. Indeed, the dead volume of the calibration chamber 2 sets the specification for gas source 4: the smaller the dead volume, the lighter the design constraints on gas source 4.

The calibration chamber 2 is gas tight so that pressure can be kept stable.

Obviously, the calibration chamber 2 is configured to allow placing a sample pressure sensor S inside the calibration chamber 2. Any opening and closing means suitable to ensure gas tightness and constant volume of the calibration chamber 2 are suitable. For instance, calibration chamber 2 may be composed of at least two parts clamped together by clamping means. Calibration chamber 2 may comprise an aperture and a tight closing mean, such as an airlock.

The calibrating device 1 also comprises a reference pressure sensor 3 configured to measure pressure inside the calibration chamber 2. The reference pressure sensor 3 may be of any type. In particular TE MS5803-14BA (manufacturer: TE Connectivity) may be used.

The calibrating device 1 further comprises a gas source 4 comprising a gas tank 41. The gas tank 41 behaves like a buffer, containing enough gas to enable one calibration without a significant pressure loss. The gas tank is filled by a compressor or a compressed air network 42. Pressure of gas inside the gas tank 41 is comprised between 6 bars and 15 bars, preferably about 10 bars.

The gas source 4 is connected to the calibration chamber 2 through a valve 5. The valve 5 controls the gas flow from the gas source 4 into the calibration chamber 2. The valve 5 may be of any type. In an embodiment, the valve 5 is a solenoid valve 51 with a flow controller 52 such as a RS 176-2113 valve (manufacturer: RS Components), controlled by an external microcontroller or a processor such as a Broadcom BCM2837B0 or a Cortex-A53 (implementing ARMv8 instruction set). A sound attenuation device 53 may be added.

In the calibrating device 1, the flow rate between the gas source and the calibration chamber is controlled by the valve 5, said valve 5 comprising a flow controller 52 having an equivalent inner diameter comprised between 2.5 mm and 3.5 mm. Controlling the flow rate instead of the pressure inside the calibration chamber is advantageous since it allows a dynamical calibration of the sample pressure sensor. Indeed, the dynamical calibration associates the variation of the signal measured by the sample pressure sensor as a result of the pressure variation undergone by said sensor to this pressure variation, for example, to mimic the variation of pressure during the gait. However, controlling the pressure, for example, via a pressure regulator, merely allows to regulate the pressure inside the chamber to keep it at a given value. Therefore, in order to dynamically calibrate the sensors, an additional controller is required to constantly adjust the settings of the pressure regulator in order to follow the pressure variation that mimics what happens during the gait. Advantageously, using the flow controller 52 for controlling the flow rate allows to set the pressure variation rate and thus to dynamically calibrate the sample pressure sensor without any additional controller. The equivalent inner diameter of the flow controller 52 may be adjusted over the whole range, either manually or by a microcontroller. With this specific valve setup, pressure inside the calibration chamber 2 is increased by a factor between 3 and 13 in one half-second. In other words, if pressure inside the calibration chamber 2 is set to 1 bar, then gas is flown into the chamber during one half-second, the final pressure inside the calibration chamber 2 will be between 3 bars and 13 bars. With the calibrating device 1 herein disclosed, increase rate of pressure is controlled by valve setup in a very versatile manner.

The whole device set-up combining the volume of the calibration chamber, the pressure of the gas inside the gas tank and the equivalent inner diameter of the flow controller as disclosed provides a flow rate, as measured under a difference of 6 bars, comprised between 3.8 and 14.8 $L \cdot s^{-1}$. This flow rate range allows to reproduce the variation of pressure undergone by sensors of an insole worn by users of different weight but also allows to reproduce the variation of pressure undergone by sensors of an insole worn by users walking at different walking speed. For example, the flow rate range allows to reproduce the variation of pressure undergone by sensors of an insole worn by a user of 75 kg walking normally when the user mass is transferred from one leg to the other one (i.e., during about 100 ms).

In an embodiment, the calibration device 1 further comprises a pressure switch 21. The pressure switch 21 is configured to allow venting of the calibration chamber 2 when pressure inside the calibration chamber 2—as measured by the reference pressure sensor 3—reaches a predetermined threshold. Thus, during calibration of a sample pressure sensor S, pressure applied cannot exceed a predetermined threshold. The threshold may be determined to avoid degradation of the sample pressure sensor S if the latter is fragile for high pressures. The threshold pressure may be comprised between 3 bars and 12 bars, preferably between 3 bars and 6 bars. The threshold may be determined with reference to the pressure of the gas source 4: indeed, as pressure inside the calibration chamber 2 increases, gas flow through the valve 5 may decrease. If pressure inside the calibration chamber 2 is always significantly less—for instance at most half—than the pressure in the gas source 4, gas flow is better controlled and pressure variation in the calibration chamber 2, i.e. the constraint on the sample pressure sensor S, is better controlled.

In an embodiment, the calibration device 1 further comprises a safety valve 22. The safety valve is configured to avoid excess pressure in the calibrating chamber 2.

When calibrating device 1 comprises a pressure switch 21 and a safety valve 22, the threshold pressure of pressure switch 21 is lower than the pressure limit defined by the safety valve 22. The safety valve 22 may be placed directly on the calibration chamber 2 or in the tubing between the valve 5 and the calibration chamber 2.

In an embodiment, the calibration chamber 2 has one longitudinal dimension longer than 30 cm. Indeed, sample pressure sensors S like insoles or straps are commonly 30 cm long and the sample pressure sensor shall be placed inside the calibration chamber 2 without being bent or otherwise under mechanical constraint. By longitudinal dimension, it is meant the longest dimension inside the calibration chamber 2: for a parallelepiped-shaped calibration chamber 2, the longitudinal dimension is the dimension of the longest edge; for an ellipsoid-shaped calibration chamber 2, the longitudinal dimension is the dimension of the longest axis. More specifically, the calibration chamber 2 has an inner area with one longitudinal dimension longer than 30 cm and one perpendicular dimension wider than 10 cm. By perpendicular dimension, it is meant a dimension perpendicular to the longitudinal dimension. In this specific embodiment, a sample pressure sensor S having an area of 30 cm×10 cm may be laid in the calibrating chamber 2 without being bent or otherwise under mechanical constraint. This configuration is especially suitable for insoles, or for a pair—right and left—of insoles.

In an embodiment, the calibration chamber 2 further comprises a gas tight membrane 23, in particular an air tight membrane. The gas tight membrane splits the calibration chamber in two compartments. The first compartment 24 comprises the reference pressure sensor 3 and gas from gas source 4 is injected in the first compartment 24. The second compartment 25 is intended to receive the sample pressure sensor S. In this configuration, the sample pressure sensor S is protected by the gas tight membrane 23 against dust or other pollutants present in the first compartment 24, for instance introduced with the pressurized gas. In addition, gas penetration in the sample pressure sensor S is prevented, which is advantageous to protect said sample pressure sensor S. If a pressure switch 21 is present, the pressure switch 21 is configured to allow venting of the first compartment 24 of the calibration chamber 2. Optionally, the second compartment 25 may comprise another pressure switch.

When the calibration chamber 2 comprises a gas tight membrane 23, the second compartment 25 may not be gas tight. In this configuration, the sample pressure sensor (S) is compressed between the casing of the second compartment 25 and the gas tight membrane 23, the latter transmitting pressure from the first compartment 24. In this configuration, the dead volume $V_0$ of the calibration chamber 2 under pressure is exactly the first compartment 24 and the calibration chamber 2 is considered as gas tight, because pressure inside the calibration chamber 2 is actually controlled and may be kept stable.

The disclosure also relates to a method of calibration for a sample pressure sensor S.

In a first step, a sample pressure sensor S is placed inside a calibration chamber 2 having a constant dead volume $V_0$ in the range of 0.1 L to 1.5 L, said calibration chamber 2 being gas tight.

In a second step, gas is injected into the calibration chamber 2 from a gas source 4 through a valve 5. The gas source 4 and the valve 5 have the features described above. The flow controller 52 has an equivalent inner diameter comprised between 2.5 mm and 3.5 mm. In an embodiment, gas is injected at a constant pressure increase rate. In this embodiment, pressure inside the calibrating chamber 2 is increasing linearly, allowing for a regular calibration over the whole range of pressure applied to the sample pressure sensor S. In an embodiment, pressure increase is controlled by a pressure switch 21 so as not to exceed a threshold value. As soon as the pressure inside the calibration chamber 2 reaches a predetermined value, typically 6 bars, the pressure switch 21 opens a vent in communication with atmosphere. With this embodiment, sample pressure sensor S is protected against excessive pressure that may be detrimental. Besides, pressure inside the calibration chamber 2 is limited, which is desirable for safety of users. In a specific embodiment, the pressure switch 21 also controls the valve 5 and stops gas injection when calibration chamber 2 is vented.

In a third step, pressure signals are acquired during injection of gas. The pressure inside the calibrating chamber 2 is measured by the reference pressure sensor 3, yielding a first signal. Simultaneously, the output of the sample pressure sensor S is measured, yielding a second signal. Thus, one measures simultaneously the pressure inside the calibrating chamber 2, i.e., the pressure applied on the sample pressure sensor S and the output of the sample pressure sensor S.

By simultaneously, it is meant that both signals are measured during the same time period. In an embodiment, both signals are measured simultaneously at a frequency comprised between 50 Hz and 200 Hz, preferably between 100 Hz and 150 Hz. In this embodiment, simultaneously means that both signal measurements are synchronized. The preferred frequency is about 110 Hz: high enough to sample about 20 points in 0.2 s, and slightly different from multiples of electrical network frequencies to avoid interferences in measurements.

The output of the sample pressure sensor S may be an electric feature of the sensor, such as resistance or capacitance, or an electric signal.

In an embodiment, both signals—from the reference pressure sensor 3 and the sample pressure sensor S—are transmitted via Bluetooth low energy (BLE) to an external computing unit.

In a fourth step, the pressure applied on the sample pressure sensor S and the output of the sample pressure sensor S are combined to determine the calibration function of the sample pressure sensor. In an embodiment, this combination is done in an external computing unit or in a computing unit comprised in the sample pressure sensor S.

In an embodiment, the sample pressure sensor S comprises a plurality of capacitive pressure cells. Capacitive pressure cells may be of any type, in particular sensors comprising a thin sheet of deformable dielectric material placed between two electrodes. Indeed, the value of the capacitance C of a capacitive pressure cell can be determined as a function of the thickness L of the dielectric sheet of the capacitive pressure cells, the surface S of the upper electrode and the lower electrode of the capacitive pressure cells and the dielectric constant & of the material between the electrodes by the following equation:

$$C = \frac{\varepsilon S}{L}.$$

Consequently, when the thickness L of the dielectric sheet of the capacitive pressure cells is changed, the capacitance C varies. Change of thickness may be induced by the pressure applied in the calibration chamber.

The sample pressure sensor S may be of any type, in particular suitable to be in contact or integrated in surfaces of seats, beds, mattresses, carpets or mats. In an embodiment, the sample pressure sensor is an insole 6, adapted to be included in a footwear. Insoles 6 are especially adapted to monitor gait and measure gait features.

Figure 2:
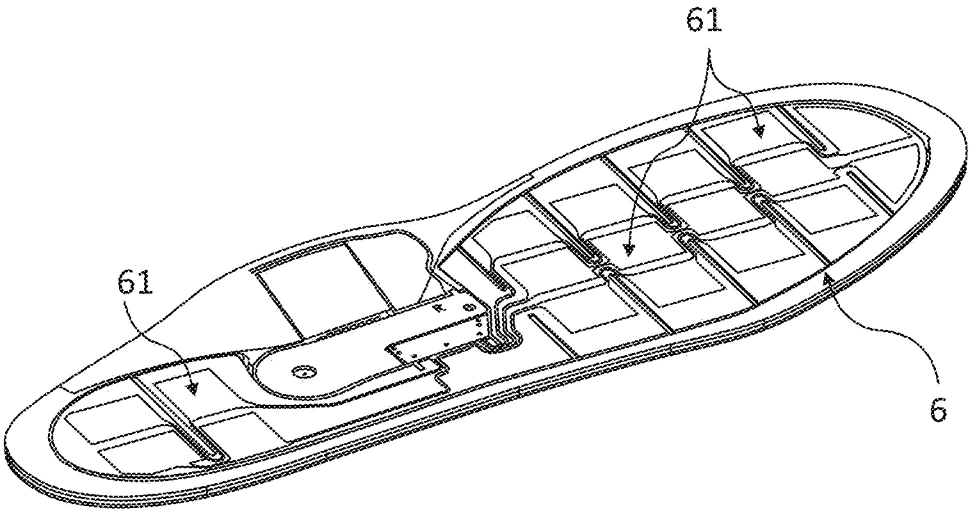
FIG. 2 is a perspective view of a sample pressure sensor in the form of an insole, suitable to be inserted into an article of footwear.

One example of this embodiment is illustrated in FIG. 2. In this example, the sample pressure sensor 6 comprises 18 capacitive pressure cells 61 distributed over a measuring area—heel and forefoot. The central part of the insole 6 comprises electrical connections and data processing unit. A bus allows for electrical connection between capacitive pressure cells 61 and data processing unit via wires.

In this embodiment, the same pressure is applied simultaneously on all capacitive pressure cells 61. And the outputs of all capacitive pressure cells 61 may be acquired simultaneously, at a frequency comprised between 50 Hz and 200 Hz, preferably between 100 Hz and 150 Hz, ideally about 110 Hz. Then, the calibration function of each capacitive pressure cell 61 may be determined and the calibration function of the insole 6 is determined based on individual calibration function of each capacitive pressure cell 61: it may be a list or a combination such as a weighted average.

In a specific embodiment, signals from reference pressure sensor 3 and all capacitive pressure cells 61 are sent via Bluetooth Low Energy (BLE) to an external computing unit, in which calibration function is determined. Then the calibration function is transmitted via BLE to the data processing unit comprised in the insole, so that calibration function is stored in the insole for further use.

In another specific embodiment, signal from reference pressure sensor 3 is sent via Bluetooth Low Energy (BLE) to the insole data computing unit, in which calibration function is determined and stored in the insole for further use.

In an embodiment, the calibration method comprises a preliminary step during which the sample pressure sensor S sends information via Bluetooth Low Energy (BLE) to the valve microcontroller. Information is defining features of the sample pressure sensor S like the dimension of samples pressure sensor—for instance the size and laterality of an insole—or technical properties of the pressure cells—type of pressure cell, maximum pressure to be applied . . . . According to this information, the microcontroller may select the equivalent inner diameter of the flow controller 52 during gas injection to adapt calibration conditions to the sample pressure sensor S. For instance, insoles of size 35 corresponds usually to people having a low weight, whereas insoles of size 45 corresponds to tall people having a greater weight. It is clear that insoles of size 45 will undergo pressures (in absolute value and in increase rate) larger than insoles of size 35. Calibration conditions may thus be adapted with a larger equivalent inner diameter of the flow controller 52 for insoles of size 45.

In an embodiment, a plurality of sample pressure sensors S is placed together inside the calibration chamber 2. Then, the same pressure is applied simultaneously on all the sample pressure sensors S. And the outputs of all sample pressure sensors S may be acquired simultaneously, at a frequency comprised between 50 Hz and 200 Hz, preferably between 100 Hz and 150 Hz, ideally about 110 Hz. Then, the calibration function of each sample pressure sensor S is determined. This embodiment is especially adapted to obtain the calibration functions of the two insoles constituting a pair of insoles—right insole and left insole.

In an embodiment, the second and third steps of the method of calibration are repeated several times. A series of measurements of the pressure applied on the sample pressure sensor S and the corresponding output of the sample pressure sensor S are obtained and used to define the calibration function. This embodiment allows to reduce measurement uncertainty and obtain more precise calibration functions for sample pressure sensors S.

EXAMPLES

The present invention is further illustrated by the following examples.

Figure 4:
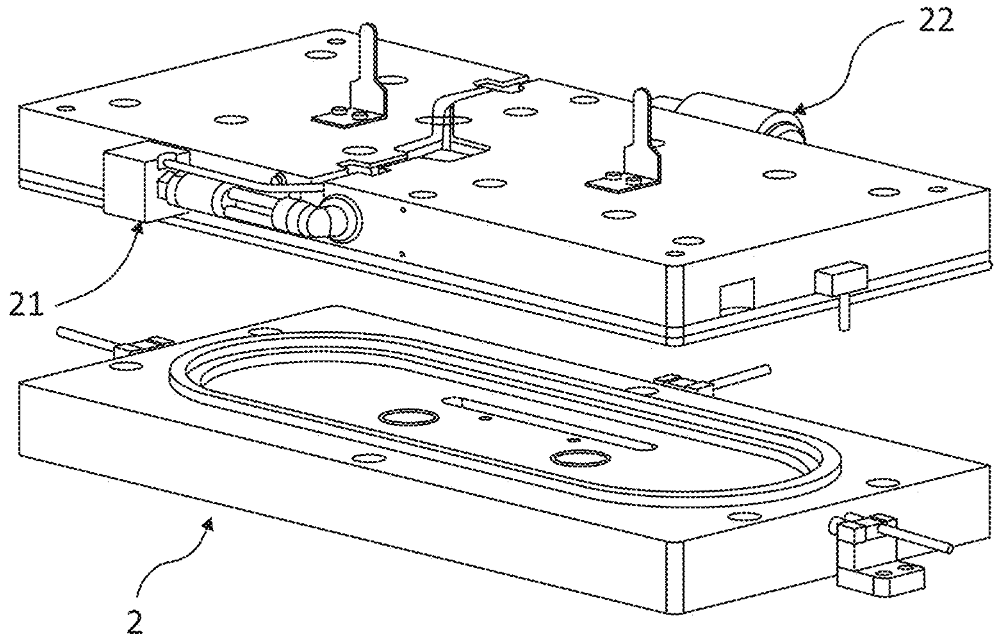
FIG. 4 is an exploded view of the calibration chamber used in examples.

A pair of insole (size 46) as shown on FIG. 2 is placed in the calibration chamber of dimensions 150×375×5 mm-0.44 L, as represented on FIG. 4. The calibration chamber is closed and then gas is injected from gas source through the valve with the flow controller adjusted with an equivalent inner diameter of 2.8 mm, corresponding to a constant variation of pressure applied of 15 $kg \cdot cm^{-2} \cdot s^{-1}$. Pressure inside the calibration chamber is measured by the reference pressure sensor with an acquisition frequency of 110 Hz. Synchronously, capacitances of all 18 capacitive pressure cells are measured with the same acquisition frequency of 110 Hz. Finally, capacitance is drawn as a function of pressure applied inside the chamber, i.e., applied on each capacitive pressure cell of the insole.

In this example, pressure increase in the calibration chamber is 15 $kg \cdot cm^{-2} \cdot s^{-1}$. This increase is typically the increase observed during a step of a 100-kg person walking normally when the person mass is transferred from one leg to the other one. Thus, calibration function of the insoles is performed in the dynamic conditions in which they will be used for gait monitoring.

Figure 3:
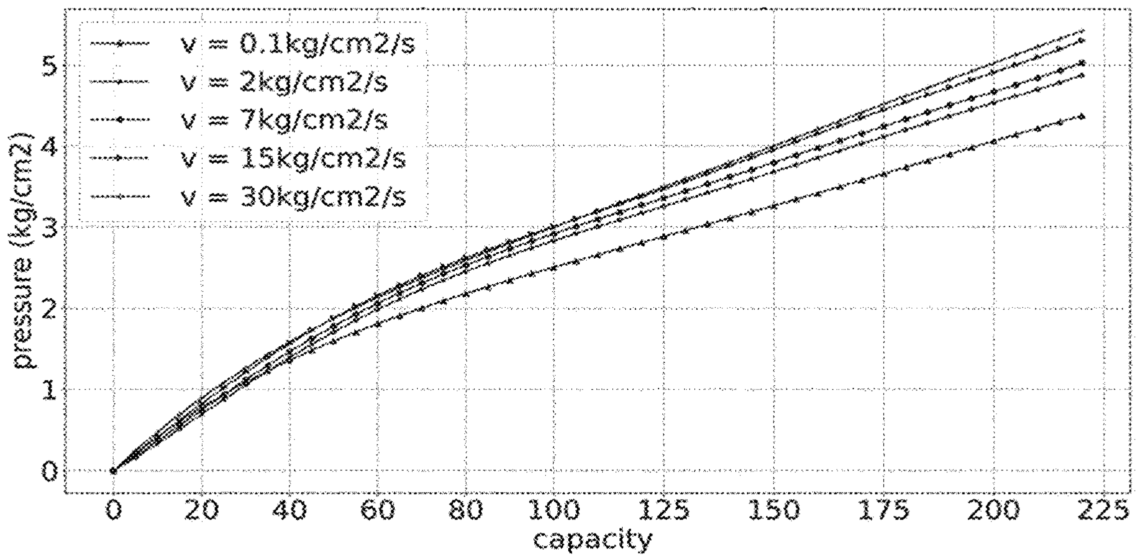
FIG. 3 is a graph showing calibration functions of some insoles corresponding to FIG. 2.

FIG. 3 shows the relationship between capacitance of said insole (arbitrary unit) and pressure applied (in $kg\cdot cm^{-2}$) with different rate of variation of pressure applied v, from 0.1 $kg\cdot cm^{-2}\cdot s^{-1}$, corresponding to static conditions to 30 $kg\cdot cm^{-2}\cdot s^{-1}$ for the highest rate of variation. From FIG. 3, one reads that for a determined pressure of 4 $kg\cdot cm^{-2}$, the capacitance of said insole decreases by 20% in dynamic conditions (capacity about 150-160) as compared to static conditions (capacity about 200). With the calibration chamber herein disclosed and allowing for measurements with variation of pressure applied v ranging from about 7 $kg\cdot cm^{-2}\cdot s^{-1}$ (equivalent inner diameter of 2.5 mm) to about 30 $kg\cdot cm^{-2}\cdot s^{-1}$ (equivalent inner diameter of 3.5 mm), calibration is obtained in dynamic conditions representative of usage conditions of insole pressure sensor, especially for gait monitoring.

The invention claimed is:

1. A calibrating device for a sample pressure sensor comprising a calibration chamber configured to allow placing the sample pressure sensor inside said calibration chamber and having a constant dead volume V0 in the range of 0.1 L to 1.5 L, said calibration chamber being gas tight;

a reference pressure sensor configured to measure pressure inside the calibration chamber; and a gas source comprising a gas tank comprising gas at a pressure comprised between 6 bars and 15 bars and connected to the calibration chamber through a valve so as to inject a controlled flow of gas into the calibration chamber;

wherein the valve comprises a flow controller having an equivalent inner diameter comprised between 2.5 mm and 3.5 mm, thereby providing with a flow rate from the gas tank to the calibration chamber measured under a difference of 6 bars comprised between 3.8 and 14.8 $L\cdot s^{-1}$.

2. The calibrating device according to claim 1, wherein the calibration device further comprises a pressure switch and/or a safety valve.

3. The calibrating device according to claim 1, wherein the calibration chamber has one longitudinal dimension longer than 30 cm.

4. The calibrating device according to claim 3, wherein the calibration chamber has one inner area with one longitudinal dimension longer than 30 cm and one perpendicular dimension wider than 10 cm.

5. The calibrating device according to claim 1, wherein the calibration chamber further comprises a gas tight membrane configured to split the calibration chamber in two compartments, the first compartment comprising the reference pressure sensor and the second compartment being configured to receive a sample pressure sensor.

6. A method of calibration for a sample pressure sensor comprising:

i) placing a sample pressure sensor inside a calibration chamber having a constant dead volume V0 in the range of 0.1 L to 1.5 L, said calibration chamber being gas tight;

ii) injecting gas from a gas source into the calibration chamber from a gas tank comprising gas at a pressure comprised between 6 bars and 15 bars through a valve comprising a flow controller having an equivalent inner diameter comprised between 2.5 mm and 3.5 mm thereby providing a flow rate measured under a difference of 6 bars comprised between 3.8 and 14.8 $L\cdot s^{-1}$;

iii) acquiring simultaneously pressure signal in the calibration chamber with a reference pressure sensor and output signal of the sample pressure sensor during injection of gas; and iv) determining the calibration function of the sample pressure sensor.

7. The method of calibration for a sample pressure sensor according to claim 6, wherein a pressure switch controls venting of the calibration chamber when pressure inside the calibration chamber reaches a predetermined threshold during injecting gas from a gas source into the calibration chamber.

8. The method of calibration for a sample pressure sensor according to claim 6, wherein pressure signals of reference pressure sensor and sample pressure sensor are measured simultaneously at a frequency comprised between 50 Hz and 200 Hz.

9. The method of calibration for a sample pressure sensor according to claim 8, wherein the frequency is comprised between 100 Hz and 150 Hz.

10. The method of calibration for a sample pressure sensor according to claim 8, wherein the frequency is at about 110 Hz.

11. The method of calibration for a sample pressure sensor according to claim 6, wherein the sample pressure sensor comprises a plurality of capacitive pressure cells and calibration function of the sample pressure sensor comprises a calibration function of each capacitive pressure cell.

12. The method of calibration for a sample pressure sensor according to claim 6, wherein the sample pressure sensor is an insole.

13. The method of calibration for a sample pressure sensor according to claim 6, wherein a plurality of sample pressure sensors is placed inside the calibration chamber and a calibration function is determined for each sample pressure sensor.

14. The method of calibration for a sample pressure sensor according to claim 6, wherein injecting gas from a gas source into the calibration chamber and acquiring simultaneously pressure signal in the calibration chamber are repeated and calibration function of the sample pressure sensor is determined from the successive pressure signals in the calibration chamber and successive output signals of the sample pressure sensor.

15. The method of calibration for a sample pressure sensor according to claim 6, wherein gas is injected from a gas source into the calibration chamber at a constant pressure increase rate.

* * * * *